(12) United States Patent
Hepworth et al.

(10) Patent No.: US 11,878,113 B2
(45) Date of Patent: Jan. 23, 2024

(54) VAPOUR PROVISION SYSTEMS

(71) Applicant: NICOVENTURES TRADING LIMITED, London (SB)

(72) Inventors: Richard Hepworth, London (GB); Patrick Moloney, London (GB); Walid Abi Aoun, London (GB)

(73) Assignee: NICOVENTURES TRADING LIMITED, London (GB)

( * ) Notice: Subject to any disclaimer, the term of this patent is extended or adjusted under 35 U.S.C. 154(b) by 495 days.

(21) Appl. No.: 16/754,502

(22) PCT Filed: Oct. 11, 2018

(86) PCT No.: PCT/GB2018/052911
§ 371 (c)(1),
(2) Date: Apr. 8, 2020

(87) PCT Pub. No.: WO2019/073238
PCT Pub. Date: Apr. 18, 2019

(65) Prior Publication Data
US 2020/0390157 A1 Dec. 17, 2020

(30) Foreign Application Priority Data
Oct. 12, 2017 (GB) ..................................... 1716732

(51) Int. Cl.
*A24F 40/46* (2020.01)
*A24F 40/51* (2020.01)
(Continued)

(52) U.S. Cl.
CPC ............. *A61M 15/06* (2013.01); *A24F 40/30* (2020.01); *A24F 40/44* (2020.01); *A24F 40/46* (2020.01);
(Continued)

(58) Field of Classification Search
CPC .................................. A24F 40/46; A24F 40/51
See application file for complete search history.

(56) References Cited

U.S. PATENT DOCUMENTS 5,598,868 A * 2/1997 Jakob ..................... A24D 1/00
131/355
5,649,554 A 7/1997 Sprinkel et al.
(Continued)

FOREIGN PATENT DOCUMENTS

CL 199600626 A1 4/1997
CN 101883596 A 11/2010
(Continued)

OTHER PUBLICATIONS

International Preliminary Report on Patentability for Application No. PCT/GB2018/052911, dated Apr. 23, 2020, 8 pages.
(Continued)

*Primary Examiner* — Russell E Sparks
(74) *Attorney, Agent, or Firm* — Burr & Forman LLP

(57) ABSTRACT

A vapor provision system includes an inhaler component and a base unit, wherein the inhaler component includes a thermal store; and the base unit includes a receiving zone for receiving the inhaler component; and a source of energy for heating the thermal store in the inhaler component when the inhaler component is located in the receiving zone such that heat from the heated thermal store is used to vaporize at least a portion of a vapor precursor material to form a vapor for inhalation by a user when the inhaler component is removed from the receiving zone.

17 Claims, 5 Drawing Sheets

(51) Int. Cl.
| | |
|---|---|
| *A61M 15/06* | (2006.01) |
| *A24F 40/44* | (2020.01) |
| *A24F 40/60* | (2020.01) |
| *A24F 40/30* | (2020.01) |
| *A24F 40/465* | (2020.01) |
| *A24F 40/10* | (2020.01) |
| *A24F 40/20* | (2020.01) |

(52) U.S. Cl.
CPC ............ *A24F 40/465* (2020.01); *A24F 40/51* (2020.01); *A24F 40/60* (2020.01); *A24F 40/10* (2020.01); *A24F 40/20* (2020.01)

(56) References Cited

U.S. PATENT DOCUMENTS

| | | | |
|---|---|---|---|
| 8,464,726 B2 * | 6/2013 | Sebastian | A24D 1/22 131/271 |
| 10,660,368 B2 * | 5/2020 | Thorens | A24F 40/465 |
| 10,758,686 B2 * | 9/2020 | Reevell | A24F 40/30 |
| 11,357,936 B2 * | 6/2022 | Lipowicz | A61M 15/0081 |
| 2009/0283103 A1 | 11/2009 | Nielsen et al. | |
| 2013/0037041 A1 | 2/2013 | Worm et al. | |
| 2014/0107815 A1 | 4/2014 | Lamothe | |
| 2014/0305820 A1 | 10/2014 | Xiang | |
| 2015/0020825 A1 | 1/2015 | Galloway et al. | |
| 2015/0101606 A1 | 4/2015 | White | |
| 2015/0136158 A1 | 5/2015 | Stevens et al. | |
| 2015/0196053 A1 | 7/2015 | Liu | |
| 2015/0208729 A1 | 7/2015 | Monsees | |
| 2015/0224268 A1 | 8/2015 | Henry et al. | |
| 2015/0272219 A1 | 10/2015 | Hatrick | |
| 2015/0320116 A1 | 11/2015 | Bleloch | |
| 2015/0327596 A1 | 11/2015 | Alarcon et al. | |
| 2015/0332379 A1 | 11/2015 | Alarcon | |
| 2016/0204637 A1 | 7/2016 | Alarcon et al. | |
| 2016/0206000 A1 | 7/2016 | Lord et al. | |
| 2016/0211693 A1 | 7/2016 | Stevens et al. | |
| 2017/0196269 A1 | 7/2017 | Bernauer | |
| 2017/0258136 A1 | 9/2017 | Hawes et al. | |
| 2018/0043114 A1 * | 2/2018 | Bowen | A61M 15/003 |
| 2018/0154103 A1 * | 6/2018 | Davis | A61M 11/041 |
| 2020/0113227 A1 | 4/2020 | McLaughlin et al. | |

FOREIGN PATENT DOCUMENTS

| | | |
|---|---|---|
| CN | 104619202 A | 5/2015 |
| CN | 204334029 U | 5/2015 |
| CN | 104983077 A | 10/2015 |
| CN | 105792687 A | 7/2016 |
| CN | 106455724 A | 2/2017 |
| CN | 206341938 U | 7/2017 |
| CN | 206403198 U | 8/2017 |
| EP | 2996504 A1 | 3/2016 |
| JP | 2005198538 A | 7/2005 |
| JP | 2006320286 A | 11/2006 |
| JP | 2013137789 A | 7/2013 |
| JP | 2014500017 A | 1/2014 |
| JP | 2014532435 A | 12/2014 |
| JP | 2015507476 A | 3/2015 |
| JP | 2015531601 A | 11/2015 |
| JP | 2016525341 A | 8/2016 |
| JP | 2017506915 A | 3/2017 |
| JP | 2017509339 A | 4/2017 |
| JP | 2017516269 A | 6/2017 |
| RU | 2517125 C2 | 5/2014 |
| RU | 2527351 C2 | 8/2014 |
| RU | 2618436 C2 | 5/2017 |
| RU | 2632634 C2 | 10/2017 |
| WO | WO-2004011067 A1 | 2/2004 |
| WO | 2009069518 A1 | 6/2009 |
| WO | WO-2014048745 A1 | 4/2014 |
| WO | 2015140554 A1 | 9/2015 |
| WO | WO-2015158482 A1 | 10/2015 |
| WO | 2015177253 A1 | 11/2015 |
| WO | WO 2015/177294 | 3/2016 |
| WO | WO-2016062777 A1 | 4/2016 |
| WO | WO-2016198266 A1 | 12/2016 |
| WO | WO-2019073238 A1 * | 4/2019 ............ A24F 40/30 |

OTHER PUBLICATIONS

International Preliminary Report on Patentability for Application No. PCT/GB2018/052912, dated Apr. 23, 2020, 8 pages.
International Search Report and Written Opinion for Application No. PCT/GB2018/052912, dated Jan. 18, 2019, 10 pages.
Notice of Reasons for Rejection for Japanese Application No. 2020-518790, dated Jul. 6, 2021, 12 pages.
Office Action dated May 12, 2022 for Colombian Application No. NC2020/0005749, 8 pages.
Office Action For Canadian Application No. 3,078,859, dated Jun. 7, 2021, 8 pages.
Office Action for Japanese Application No. 2020-518790, dated Jun. 25, 2021, 29 pages.
Office Action For Japanese Application No. 2020-520247, dated Jul. 6, 2021, 14 pages.
Office Action For Russian Application No. 2020112259, dated Feb. 3, 2021, 10 pages.
Search Report for Russian Application No. 2020112315 dated Nov. 17, 2020, 2 pages.
International Search Report and Written Opinion, Application No. PCT/GB2018/052911, dated Jan. 18, 2019, 13 pages.
Office Action received for Chinese Patent Application No. 2018800663612, dated Apr. 22, 2022, 13 pages (10 pages of English Translation and 3 pages of Official Copy).

* cited by examiner

VAPOUR PROVISION SYSTEMS

PRIORITY CLAIM

The present application is a National Phase entry of PCT Application No. PCT/GB2018/052911, filed Oct. 11, 2018, which claims priority from GB Patent Application No. 17167321.1, filed Oct. 12, 2017.

FIELD

The present disclosure relates to vapor provision systems such as nicotine delivery systems (e.g. electronic cigarettes and the like).

BACKGROUND

Conventional vapor provision systems for generating a vapor for user inhalation, such as electronic cigarettes (e-cigarettes), typically include the following main components:
(i) a vapor precursor material from which the vapor is generated;
(ii) a vaporizer for generating vapor from the vapor precursor material in a vapor generation region, e.g. through heat vaporization;
(iii) control circuitry for controlling the operation of the vaporizer, e.g. including a sensor for activating the vaporizer, such as a button or puff sensor, and also in many cases a microcontroller for providing additional functionality; and
(iv) a power supply, typically a rechargeable battery, for driving the vaporizer.

During use, a user inhales on a vapor outlet (mouthpiece) for the system while electrical power is supplied to the vaporizer to vaporize a portion of the vapor precursor material. Air is drawn into the device through inlet holes and into the vapor generation region where it mixes with the vaporized precursor material and forms a condensation aerosol. The mixture of air and vapor/condensation aerosol is drawn along an outlet flow path from the vapor generation region to the mouthpiece for inhalation by the user.

Vapor provision systems often, though not always, comprise a modular assembly including both a reusable part and a replaceable cartridge part. Typically the replaceable cartridge part will comprise the vapor precursor material and the vaporizer and the reusable device part will comprise the power supply (rechargeable battery) and control circuitry. It will be appreciated these different parts may comprise further elements depending on functionality. For example, the reusable device part may comprise a user interface for receiving user configuration input and for displaying operating status characteristics, and the replaceable cartridge part may comprise a temperature sensor for helping to regulate the vaporization temperature.

Cartridges are electrically and mechanically coupled to a control unit for use, for example using a screw thread or bayonet fixing with appropriately engaging electrical contacts. When the vapor precursor material in a cartridge is exhausted, or the user wishes to switch to a different cartridge having a different vapor precursor material, a cartridge may be removed from the control unit and a replacement cartridge attached in its place.

Vapor provision systems are in some respects relatively complex devices which are often significantly larger than conventional cigarettes and can be costly to produce. In many cases this is warranted having regard to the desired functionality, for example in terms of operating features and capacity. However, the inventors have recognized there are also situations in which a simpler form of device may be preferred, for example to provide a relatively low-cost one-time use type of disposable device (e.g. lasting for a similar time to a conventional combustible cigarette) that may be made readily available for users who might not wish to carry a more conventional electronic cigarette, or whose usual device is out of power or has been forgotten. There are also users who would, at least on some occasions, prefer to use a vapor provision system which is more similar in size to a conventional combustible cigarette.

Various approaches are described which seek to help address or mitigate at least some of these issues.

SUMMARY

According to a first aspect of certain embodiments there is provided a vapor provision system comprising: an inhaler component and a base unit, wherein the inhaler component comprises a thermal store; and the base unit comprises: a receiving zone for receiving the inhaler component; and a source of energy for heating the thermal store in the inhaler component when the inhaler component is located in the receiving zone such that heat from the heated thermal store is used (e.g. by conduction or radiation) to vaporize at least a portion of the vapor precursor material to form a vapor for inhalation by a user when the inhaler component is removed from the receiving zone.

According to a second aspect of certain embodiments there is provided a base unit for use in the vapor provision system of the above-mentioned first aspect of certain embodiments.

According to a third aspect of certain embodiments there is provided an inhaler component for use in the vapor provision system of the above-mentioned first aspect of certain embodiments.

According to a fourth aspect of certain embodiments there is provided a method of generating a vapor in a vapor provision system comprising an inhaler component and a base unit, wherein the inhaler component comprises a thermal store and the base unit comprises a receiving zone for receiving the inhaler component and a source of energy for heating the thermal store in the inhaler component, wherein the method comprises using the source of energy to heat the thermal store when the inhaler component is located in the receiving zone, removing the inhaler component from the receiving zone, and using heat from the thermal store to heat a vapor precursor material to form the vapor for inhalation by a user after the inhaler component has been removed from the receiving zone.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to vapor provision systems, which may also be referred to as aerosol provision systems, such as e-cigarettes. Throughout the following description the term "e-cigarette" or "electronic cigarette" may sometimes be used; however, it will be appreciated this term may be used interchangeably with vapor (aerosol) provision system and electronic vapor (aerosol) provision system. Furthermore, and as is common in the technical field, the terms "vapor" and "aerosol", and related terms such as "vaporize" and "aerosolize", may also be used interchangeably.

Figure 1A:
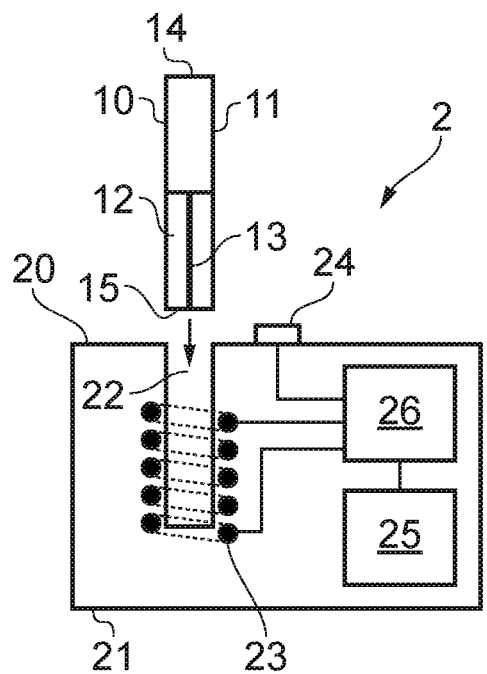
FIGS. 1A to 1C represent in highly schematic cross-section a vapor provision system in accordance with certain embodiments of the disclosure at different stages of use.
Figure 1B:
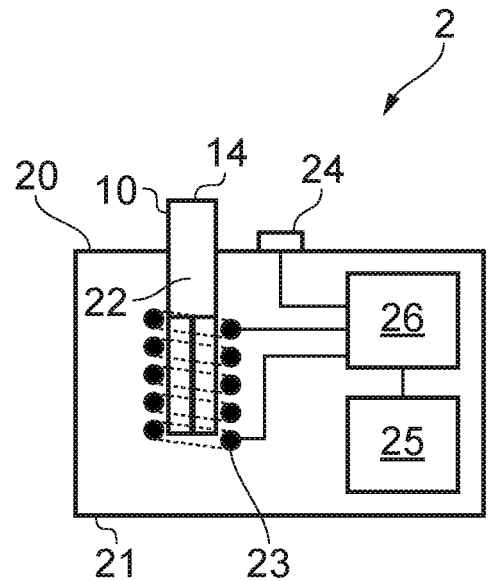
Figure 1C:
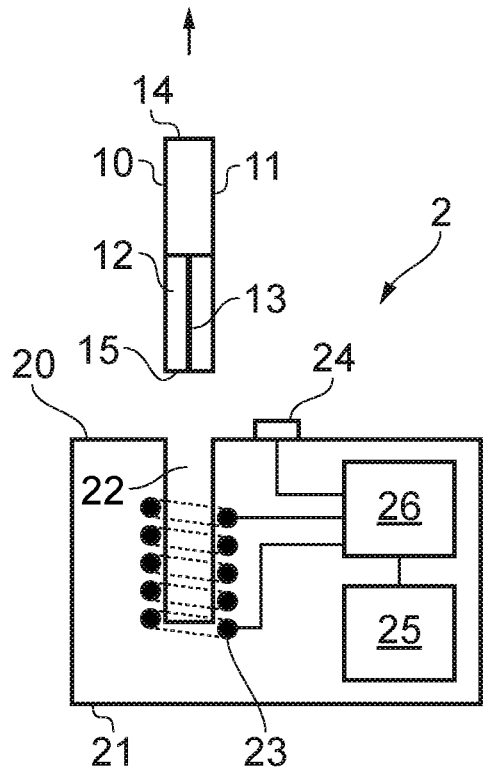

FIGS. 1A to 1C represent in highly schematic cross-section a vapor provision system 2 in accordance with certain embodiments of the disclosure at different stages of use. The system 2 represented here comprises two main components, namely an inhaler component 10 and a base unit 20. As discussed further herein, the inhaler component 10 may be placed in (or in other embodiments on) the base unit 20 to prepare it for use (i.e. to initiate vapor generation), and then removed from the base unit for use (i.e. for user inhalation of the generated vapor).

The inhaler component 10 comprises a generally tubular housing 11 defining an air flow path between an air inlet 15 and a mouthpiece outlet 14. Within the housing 11 there is a source of vapor precursor material 12 arranged in/adjacent to the air flow path and a thermal store 13 in thermal contact with part of the vapor precursor material 12. There are various configurations which may be adopted for the arrangement of the vapor precursor material 12 and the thermal store 13 as discussed further below. For example, the vapor precursor material may comprise a solid, gel or foam material rather than, or in addition to, a liquid material. However, in this example the source of vapor precursor material comprises a liquid vapor precursor material retained by an absorbent/wadding material, e.g. organic cotton or other porous material, such as a fiberglass material or a porous metal or ceramic material, and the thermal store comprises a volume of metal, for example formed from a portion of sheet steel.

The tubular housing 11 in this example has a size which broadly corresponds with a conventional cigarette, for example having a length of around 100 mm and a diameter of around 7 mm. The internal diameter of the tubular housing may, for example, be around 5 mm. The housing 11 may in this example comprise a plastics material, but in other examples may comprise a card/paper material. Generally, the housing may be formed of any material, but there will typically be a desire for the housing to be made relatively cheaply given it will typically be intended to be a disposable item. The housing may be arranged to present an outer surface that mimics the appearance of a conventional cigarette, for example having a white color along the majority of its length with a brown section towards the mouthpiece outlet 14 representing a conventional cigarette filter section. However, it will be appreciated the aesthetic appearance of the inhaler component, as well as its specific shape, dimensions and material, are not of fundamental significance to the principles described herein.

As noted above, the vapor precursor material in this example comprises a vaporizable liquid retained by an absorbent/wadding material. In this example the wadding material comprises organic cotton, but in other examples the wadding material may comprise other absorbent materials, for example fiberglass, steel wool, paper, ceramic fibers, tobacco material and so forth. The liquid is of a type conventionally used in electronic cigarettes, for example comprising an amount of nicotine, e.g. around 3% nicotine, and a base liquid comprising around 50% glycerol and roughly equal measures of water and propylene glycol. The liquid may further comprise other components, such as a flavoring. In some examples a liquid having a relatively low vaporization temperature may be selected, for example, a liquid comprising a relatively large amount of ethanol or triacetin. It will be appreciated the specific liquid used in a given implementation may be a matter of user preference, for example by providing a range of inhaler components having vapor precursor materials with different characteristic, e.g. in terms of nicotine content and/or flavor, from which a user may select.

The thermal store in this example comprises a generally rectangular shape pressed from a sheet of steel and comprises, e.g. AISI type 430 or 409 steel, with dimensions of around 25 mm×3 mm×0.1 mm. However, other forms of thermal store may be adopted in other implementations, for example comprising different materials, e.g. conductive ceramic, other metals or alloys, e.g. comprising aluminum and/or iron and/or nickel, graphite and so on, and different shapes and sizes. For example, rather than having a generally flat shape, the thermal store in other implementations may have a tubular shape, for example in the form of a solid or hollow pin/rod or in the form of a helical or flat coil. As discussed herein, heat in the thermal store may be used to heat and vaporize a portion of vapor precursor material for inhalation. A relatively large thermal mass for the thermal store will mean more vapor precursor material may be vaporized but can be expected to take longer to heat. On the other hand, a relatively small thermal mass for the thermal store will allow more rapid heating, but with less vapor generation before the thermal mass cools. Thus, for a given implementation, the thermal mass for the thermal store may be selected according to the desired properties in terms of balancing the rate of heating and the amount of vapor that can be vaporized for each use. As discussed further herein, the thermal store 13 in the example implementation represented in FIGS. 1A to 1C may be inductively heated by the base unit 20. In that regard the thermal store may also be referred to as a susceptor and comprise any material susceptible to inductive heating (e.g. a ferritic or martensitic steel). In other examples the thermal store 13 may be heated by the base unit 20 by means other than inductive heating, e.g. conductive and/or radiative heating, and in such cases the thermal store 13 need not comprise a material that is susceptible to inductive heating.

Turning now to the base unit 20, this is schematically represented in FIGS. 1A to 1C as having a generally rectangular box-like shape, but in practice the overall shape of the base unit is of no particular significance, and may, for example, be chosen according to a desired aesthetic appearance, for example, the base unit may equally be configured with an appearance which are generally similar to an ashtray or may be generally flat, in the form of a mat. It will also be appreciated the base unit may not be a stand-alone device, but may be incorporated into another apparatus. For example, the base unit may be incorporated into a vehicle, for example with an appearance similar to a conventional cigarette lighter socket. It may be expected the base unit 20 will for many implementations comprise a relatively fixed installation, for example it may be fixed to a table or wall in a public place and be provided with mains power. However, in other implementations the base unit may be a portable device having an internal power supply and sized to allow it to be conveniently carried by a user.

The base unit 20 in this example comprises an outer housing 21 in which is defined a receiving zone 22 that is sized and shaped to receive at least a portion of the inhaler component 10, a power supply 25, control circuitry 26, an activation sensor 24, and an inductive coil 23.

In this example the receiving zone 22 is defined by a generally cylindrical recess in a top wall of the base unit 20. The cylindrical recess has a diameter which is a little larger than the diameter of the housing 10 of the inhaler component and a depth which allows the end of the inhaler component containing the susceptor 13 to be fully received in the cylindrical recess, as schematically represented in FIG. 1B. It will be appreciated this provides merely one example of a suitable size and shape for the receiving zone, and other arrangements may be adopted in other implementations. For example, in some implementations the receiving zone may not comprise any recess or opening in a surface of the base unit, but may simply comprise an area on an outer surface of the base unit against which the inhaler component 10 is placed.

The power supply 25 is arranged to provide operating power for the base unit 20. As noted above, for a portable base unit the power supply 25 may comprise a battery, e.g. a rechargeable lithium-ion battery. However in this example it is assumed the base unit 20 is intended for use in a generally fixed installation and receives external power, for example from a mains power supply. Thus, the power supply 25 in this example corresponds with a power circuit connected to an external mains power supply and arranged to convert the external mains power supply to a power supply suitable for operating the base unit, for example a 12 V DC power supply. It will, of course, be appreciated the particular nature of the power supply on which the base unit operates is not significant to the principles described herein. For example, in other implementations the base unit could be powered by a fuel cell or solar power (e.g. in the case of a base unit intended for outside use, such as in the vicinity of a bus stop).

The control circuitry 26 is configured to control the operation of the base unit 20 to provide the functionality described herein in accordance with embodiments of the disclosure. The control circuitry (processor circuitry) may comprise various sub-units/sub-circuits for providing this functionality and may be implemented as a number of discrete hardware elements and/or as appropriately configured functions of the control circuitry. Thus the control circuitry may comprise circuitry which is suitably configured/programmed to provide the desired functionality using conventional programming/configuration techniques for operating electronic devices. It will be appreciated the functionality of the control circuitry 26 can be provided in various different ways, for example using one or more suitably programmed programmable computer(s), or one or more suitably configured application-specific integrated circuit(s)/circuitry/chip(s)/chipset(s).

The inductive heater coil 23 is arranged so as to inductively heat the susceptor 13 in an inhaler component received in the receiving zone 22 when the inductive heater coil 23 is activated by the control circuitry. Thus, in the configuration of FIGS. 1A to 1C, the inductive heater coil comprises a helical coil wound around the cylindrical recess comprising the receiving zone over a portion that surrounds the susceptor 13 when the inhaler component is in the receiving zone. Thus, when the inhaler component 10 is received in the receiving zone 22 and the inductive heater coil 23 is driven to induce current in the susceptor 13, the susceptor is heated. The operating characteristics of the inductive heater coil 23, for example in terms of the number of turns, current and frequency of operation, may be selected having regard to the well understood principles of inductive heating taking account of the particular susceptor geometry adopted in a given implementation. In this regard, the inductive heater coil may, for example, be designed so as to heat the susceptor/thermal store in the inhaler component to a temperature of around 200° on a timescale on the order of a few seconds.

The activation sensor 24 is configured to provide an indication to the control circuit 26 when it should apply current to the inductive heater coil 23. In effect, the role of the activation sensor is to indicate to the control circuitry when an inhaler component currently in the receiving zone is about to be removed for use so that the control circuitry 26 should drive the inductive coil to heat the susceptor/thermal store in the inhaler component so that it is ready for use. The activation sensor 24 may be based on a range of different technologies in different implementations. For example, in some cases the activation sensor may comprise a motion sensor configured to detect movement of the inhalation component as a user starts to withdraw the inhalation component from the receiving zone. In some other cases the activation sensor may comprise a proximity sensor configured to detect the approach of a user's hand when the user is about to withdraw the inhaler component from the receiving zone. In yet other cases, the activation sensor may comprise a switch which is manually activated by a user to indicate they are about to withdraw the inhalation opponent from the receiving zone. In yet other cases, the activation sensor may be configured to simply detect when an inhaler component is inserted into the receiving zone, such that the inductive heater coil is activated whenever an inhaler component is placed in the receiving zone. Regardless of the specific manner in which the activation sensor is configured to detect when the control circuitry should drive the inductive heating coil 23, it may be implemented having regard to conventional sensing techniques. That is to say, it may be based on conventional techniques (e.g. using capacitive or optical sensing technologies for detecting the approach, presence or movement of an object according to the implementation at hand, or a conventional mechanical switch for manual activation). In some implementations the base unit might not comprise an activation sensor, and instead the induction coil may instead be permanently driven so that whenever an inhaler component is inserted in the base unit it is inductively heated. In another example, the base unit may be configured to receive the inhaler component in a first position, and then when a user moves the inhaler component to a second position (e.g. pushing down against a spring force or simply repositioning the inhaler component relative to the base unit), the inductive heating coil may be activated to heat the thermal store. In one example, the inhaler component may be configured to "pop up" after a given amount of time of heating, e.g. based on a timer or thermally responsive latch releasing a spring force, to indicate when the thermal store has been sufficiently heated for use. In some cases the base unit may comprise a second coil for detecting the motion of the susceptor/heat store as it starts to be removed from the base unit and the inductive heating coil driven accordingly.

Having discussed the overall structure and configuration of the vapor provision system 2 represented in FIGS. 1A, 1B and 1C, an example use of the system 2 will now be described. In this regard it is assumed FIG. 1A schematically represents a situation in which an un-used inhaler component is about to be used. Thus, in FIG. 1A the inhaler component 10 is shown on approach to the receiving zone 22 of the base unit 20. At this stage the susceptor/heat store 13 in the un-used inhaler component 10 is cold (i.e. at ambient temperature).

FIG. 1B shows the inhaler component 10 when it is received in the receiving zone 22 of the base unit 20. As discussed above, in this arrangement, the inductive heater coil 23 in the base unit 20 surrounds the susceptor 13 in the inhaler component 10. While the inhaler component 10 is located in the receiving zone as represented in FIG. 1B, the activation sensor 24 detects that the susceptor 13 in the inhaler component should be heated because it is about to be removed for use. As noted above, this detection may be based on different sensor technologies according to the implementation at hand. In this example it is assumed the activation sensor 24 is a motion sensor configured to detect motion of the inhaler component when a user starts to withdraw the inhaler component for use.

When the activation sensor 24 determines the susceptor 13 in the inhaler component should be heated, a signal is passed to the control circuitry 26, in response to which the control circuitry applies a drive signal to the inductive heating coil 23 by appropriately directing power from the power supply 25 to the coil. The application of a drive signal to the inductive heater coil 23 induces currents in the susceptor 13, thereby heating the susceptor. In this example the inductive heater coil 23 is configured to heat the susceptor to a temperature of around 200° within two seconds. It will be appreciated the characteristics of the drive signal applied to the inductive heater coil 23 to achieve this rate of heating will depend on the susceptibility of the susceptor to induced currents and its thermal mass (i.e. the size of the thermal store 13). However, as noted above, the operation of the inductive heater coil may be in accordance with conventional inductive heater techniques.

In this example in which the inductive heating is triggered by the activation sensor 24 detecting the inhaler component 10 is being withdrawn from (i.e. starts moving away from) the receiving zone, a user of the vapor provision system 2 may be made aware of a need to withdraw the inhaler component 10 from the receiving zone relatively slowly to allow time for the susceptor to be heated as it is withdrawn. In some cases an indicator, for example a light, may be provided to indicate when the induction heater coil 23 is being driven. Thus, when the control circuitry determines that sufficient energy has been transferred to the susceptor 13 in the inhaler component (e.g. after a predetermined amount of time of driving the induction heating coil), the indicator light may switch off. Thus, when a user starts to withdraw the inhaler component 10 from the receiving zone they will see the indicator light illuminate and understand they should delay withdrawing the inhaler component until after the indicator light goes out. If there is a concern for a given implementation that an approach based on triggering the heater coil in response to the base unit determining when the inhaler component starts to be withdrawn will not give sufficient time to heat the susceptor without requiring a delay which may frustrate a user, a different activation sensor approach may be adopted. For example, a proximity sensor approach based on detection of a user's hand approaching the base unit as discussed above may be used instead. In this case the activation of the heating coil 23 can begin before the user starts to remove the inhaler component from the base unit, thereby helping reduce any user-perceived delay.

FIG. 1C schematically represents the inhaler component 10 having been removed from the base unit 20 after the susceptor/thermal store 13 has been heated by the inductive coil 23. At this stage the inhaler component 10 is ready for user inhalation in that a user may inhale on the mouthpiece end 14 to draw air in through the inlet 15 and along the airflow path defined by the housing 11. As the user is doing this, the heat in the thermal store 13 vaporizes a portion of the vapor precursor material 12 through thermal conduction so the resulting vapor becomes entrained in the airflow through the inhaler component and is inhaled by a user through the mouthpiece 14. In some configurations the organic cotton holding the liquid air vapor precursor material may be sufficiently loose that air can be drawn through the wadding, and in some other configurations an air channel may be provided by a passageway through the wadding in the vicinity of the susceptor to allow air to be drawn through the inhaler component primarily in the region where the vapor is being generated by the thermal store 13.

Having taken a puff on the inhaler component and inhaled a portion of the vapor, the user may in some cases continue to hold the inhaler component ready for a second puff in the event the thermal store has sufficient heat capacity to retain a temperature which is sufficient to continue to vaporize enough vapor precursor material for a second (and potentially further) puffs. In other cases the thermal store may be sufficient to provide only one puff, so that when a user has taken a puff, the inhaler component may be returned to the receiving zone ready to be re-heated for the next puff in the same way as discussed above. A user may continue to puff on the inhaler component, reheating as necessary, until the vapor precursor material is exhausted. After this time the inhaler component may be discarded and a new inhaler component used, although in principle the inhaler component may also be refilled. For example, it may be dipped in a pool of liquid vapor precursor material so that the cotton wadding absorbs a portion of the liquid to in effect refill the inhaler component with vapor precursor material for further use. In some examples a pool/reservoir of vapor precursor material may be provided within the base unit such that when an inhaler component is received in the receiving zone, a part of the inhaler component, for example an end, is in contact with the reservoir of vapor precursor material. Thus, not only does the base unit provides the inhaler component with heat to vaporize the vapor precursor material, the base unit may also provide the inhaler component with the vapor precursor material itself. In that sense the inhaler components may be initially supplied without any vapor precursor material. Furthermore, in some cases the inhaler component may be configured to absorb an amount of liquid corresponding to a single puff which may be vaporized while the inhaler component is still in the receiving zone of the base unit, with the vaporized material remaining in the inhaler component until it is withdrawn and inhaled by a user.

It may be expected one use scenario would be for a base unit to be provided in a public space, for example in a restaurant, bar or area where people frequently wait, such as a bus stop, and users may simply buy individual or packets of inhaler components to be used on a disposable basis in conjunction with such "public" base units. For example, the base unit may be provided by a manufacturer/supplier of the inhaler components. In that regard, the inhaler components and base units may be configured only to operate together, for example by requiring a specific shape for the inhaler component to match a specific shape of the base unit or using other identification means, for example an RFID tag in each inhaler component to identify it as an inhaler component which may be used with the relevant base unit(s). This approach therefore provides users with the ability to inhale vapor of the kind provided by electronic cigarettes without needing a complete standalone device (i.e. a device with a battery and control electronics of their own). This may be desired for a number of reasons. For example a user may simply not wish to carry a bulkier standalone device. A user may have their own device, but have forgotten to take it with them, and so may wish to purchase a pack of the disposable inhaler components for use with a public base unit in the interim. In yet another scenario, a user may have their own electronic cigarette, but simply want to try a new flavor provided as a disposable inhaler component of the kind described above, for example by way of a sample test.

Figure 2:
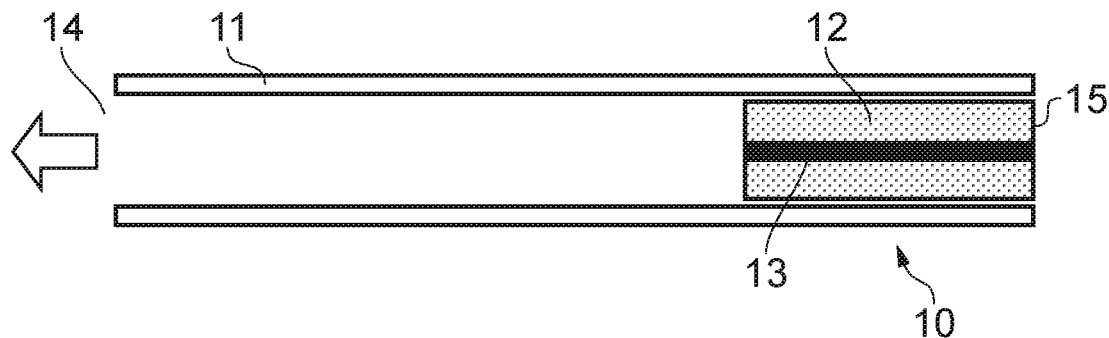
FIGS. 2 to 11 represent in highly schematic cross-section an inhaler component of a vapor provision system in accordance with certain embodiments of the disclosure.

FIG. 2 schematically represents in cross-section view the inhaler component discussed above with reference to FIGS. 1A to 1C.

Figure 3:
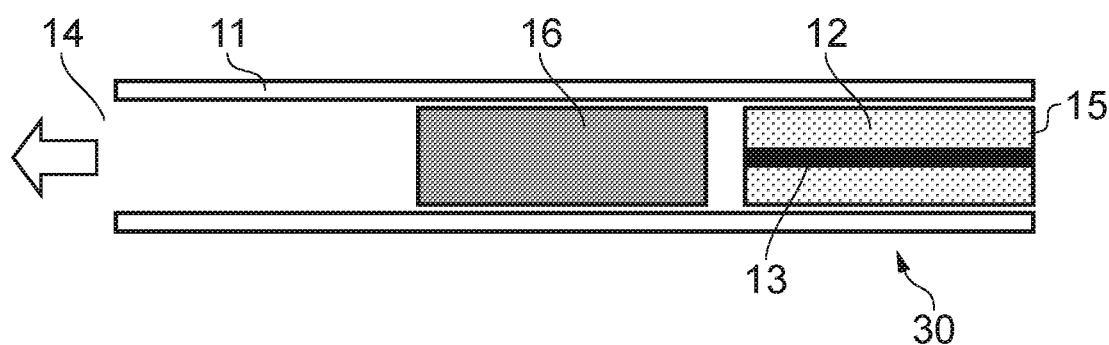

FIG. 3 represents in schematic cross-section view an inhaler component 30 that is a variation of the inhaler component 10 discussed above with reference to FIGS. 1A to 1C and shown in FIG. 2. Elements of the inhaler component 30 represented in FIG. 3 which are functionally similar to, and will be understood from, corresponding elements of the inhaler component 10 represented in FIG. 2 are identified with corresponding reference numerals and are not discussed again in the interests of brevity. The inhaler component 30 differs from the inhaler component represented in FIG. 2 by the addition of a portion of tobacco 16 within the housing 11. The tobacco portion 16 may comprise a section of loose cut tobacco arranged on a downstream side of the vapor precursor material 12 and thermal store 13 (i.e. between the vapor precursor material and the mouthpiece) so that vapor generated from the vapor precursor material is drawn through the tobacco 16 before inhalation. This can help provide a user with additional flavor characteristics that may be desired in some cases. The inhaler component 30 of FIG. 3 may be used in conjunction with a base unit corresponding to that used with the inhaler component 10 of FIG. 2 and discussed above.

Figure 4:
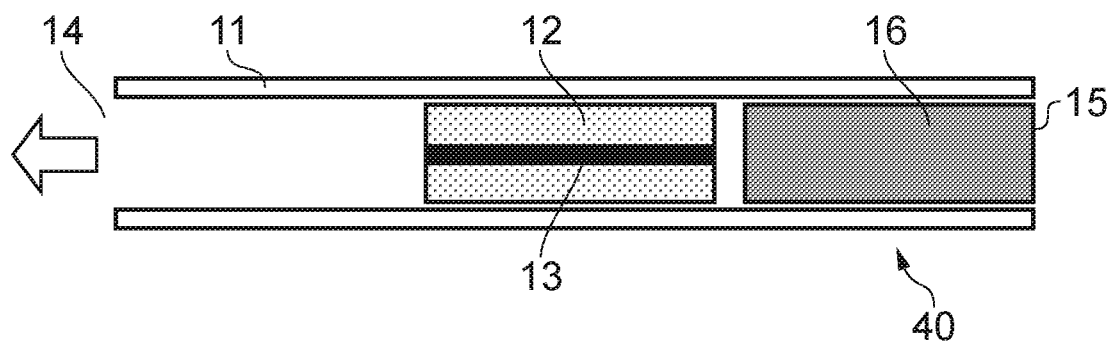

FIG. 4 represents in schematic cross-section view an inhaler component 40 that is another variation of the inhaler component 10 discussed above with reference to FIGS. 1A to 1C and shown in FIG. 2. Elements of the inhaler component 40 represented in FIG. 4 which are functionally similar to, and will be understood from, corresponding elements of the inhaler component 10 represented in FIG. 2 are identified with corresponding reference numerals and are not discussed again in the interests of brevity. The inhaler component represented in FIG. 4 differs from the inhaler component represented in FIG. 2 by the addition of a portion of tobacco 16 within the housing 11. The tobacco portion 16 is arranged on an upstream side of the vapor precursor material 12 and thermal store 13 (i.e. the vapor precursor material is between the tobacco portion and the mouthpiece) so that air entering the inhaler component is drawn through the tobacco 16 before passing the vapor precursor material. This can help provide a user with additional flavor characteristics that may be desired in some cases. The inhaler component 40 of FIG. 4 may be used in conjunction with a base unit corresponding to that used with the inhaler component 10 of FIG. 2 and discussed above, albeit with the cylindrical recess defined by the receiving zone being made sufficiently deep for the portion of the inhaler component having the susceptor to be located adjacent the inductive heating coil in the base unit.

Figure 5:
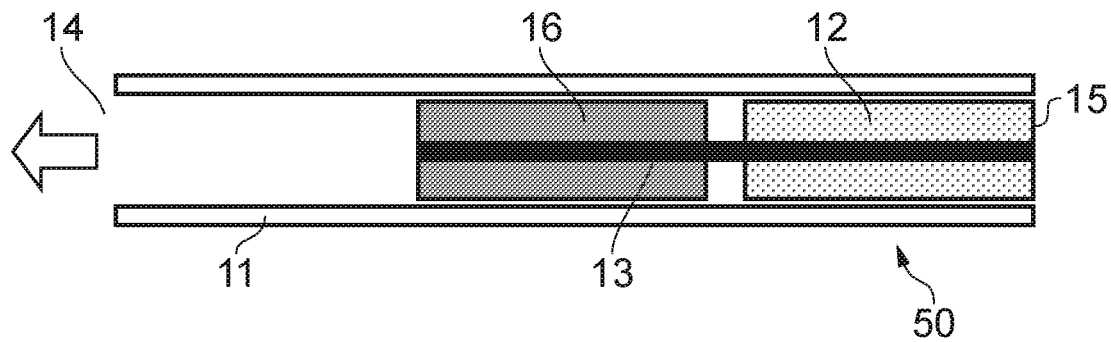

FIG. 5 represents in schematic cross-section view an inhaler component 50 that is a variation of the inhaler component 30 discussed above and shown in FIG. 3. Elements of the inhaler component 50 represented in FIG. 5 which are functionally similar to, and will be understood from, corresponding elements of the inhaler component 30 represented in FIG. 3 are identified with corresponding reference numerals and are not discussed again in the interests of brevity. The inhaler component represented in FIG. 5 differs from the inhaler component represented in FIG. 3 by virtue of the thermal store/susceptor 13 having an extent that places it in thermal contact with both the liquid vapor precursor material 12 and the tobacco portion 16. Accordingly, in use the tobacco portion 16, as well as the vapor precursor material 12 are both heated by the thermal store. In that sense the tobacco portion 16 may itself be considered a part of the inhaler component's vapor precursor material (i.e., FIG. 5 represents an example in which the vapor precursor material comprises both a liquid and a solid). In a variation on this approach, the liquid vapor precursor material and the tobacco portion may be associated with separate susceptors (as opposed to a single susceptor spanning both of them) which can be separately heated by the base unit. The inhaler component 50 of FIG. 5 may be used in conjunction with a base unit corresponding to that used with the inhaler component 10 of FIG. 2 and discussed above, albeit with the cylindrical recess defined by the receiving zone and the induction heating coil being made sufficiently large for the portion of the inhaler component having the susceptor to be located adjacent the inductive heating coil(s) in the base unit.

Figure 6:
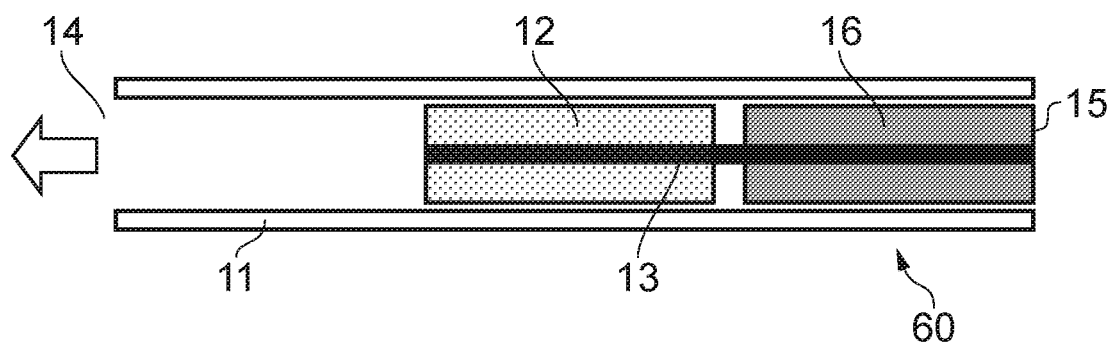

FIG. 6 represents in schematic cross-section view an inhaler component 60 that is a variation of the inhaler component 50 discussed above and shown in FIG. 5. Elements of the inhaler component 60 represented in FIG. 6 which are functionally similar to, and will be understood from, corresponding elements of the inhaler component 50 represented in FIG. 5 are identified with corresponding reference numerals and are not discussed again in the interests of brevity. The inhaler component represented in FIG. 6 differs from the inhaler component represented in FIG. 5 by virtue of the liquid vapor precursor material 12 and the tobacco portion (solid vapor precursor material) 16 being swapped in their relative positions along the airflow path between the air inlet 15 and the mouthpiece outlet 14. The inhaler component 60 of FIG. 6 may be used in conjunction with a base unit corresponding to that used with the inhaler component 10 of FIG. 2 and discussed above, albeit with the cylindrical recess defined by the receiving zone and the induction heating coil being made sufficiently large for the portion of the inhaler component having the susceptor to be located adjacent the inductive heating coil(s) in the base unit.

Figure 7:
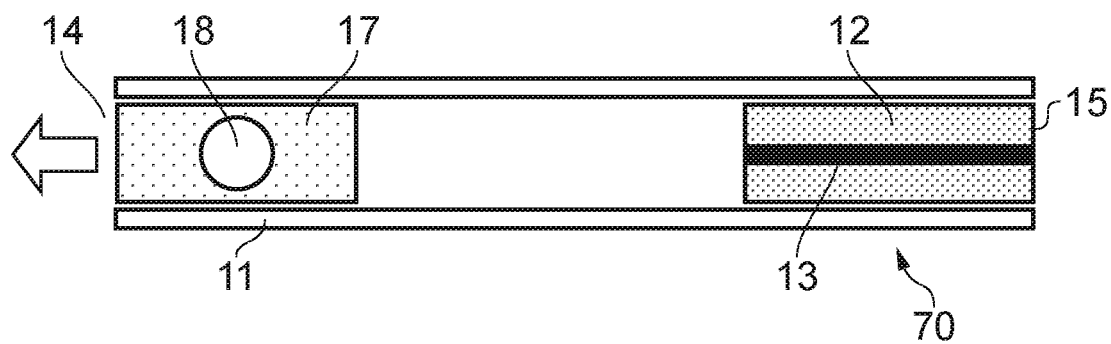

FIG. 7 represents in schematic cross-section view an inhaler component 70 that is a variation of the inhaler component 10 discussed above with reference to FIGS. 1A to 1C and shown in FIG. 2. Elements of the inhaler component 70 represented in FIG. 7 which are functionally similar to, and will be understood from, corresponding elements of the inhaler component 10 represented in FIG. 2 are identified with corresponding reference numerals and are not discussed again in the interests of brevity. The inhaler component represented in FIG. 7 differs from the inhaler component represented in FIG. 2 by the addition of a filter section 17 within the airflow path adjacent the mouthpiece opening 15. The filter section 17 may, for example, comprise a filter material of the type used in any conventional cigarette, e.g. cellulose acetate. Furthermore, the filter section 17 includes a flavor capsule 18 which may be selectively broken by a user to allow flavorant within the capsule to absorb within the filter and impart flavor characteristic to the vapor provided by the inhaler component. For example, the flavor capsule 18 may comprise a breakable shell containing a liquid containing menthol, or other, flavorant. In this regard, the flavor capsule 18 may correspond, e.g. in terms of its material structure and contents, with the types of flavor capsules commonly used in conjunction with conventional cigarettes. The inhaler component 70 of FIG. 7 may be used in conjunction with a base unit corresponding to that used with the inhaler component 10 of FIG. 2 and discussed above. More generally, it will be appreciated the inhaler component may be provided with other means for modifying the organoleptic properties of the output from the inhaler component, e.g. by filtering or adding flavorings.

It will further be appreciated there are various different ways in which the vapor precursor material and thermal store can be provided in addition to approaches based on liquid-soaked wadding and a planar susceptor such as in some of the example discussed above. Some alternative configurations are schematically represented in FIGS. 8 to 10.

Figure 8:
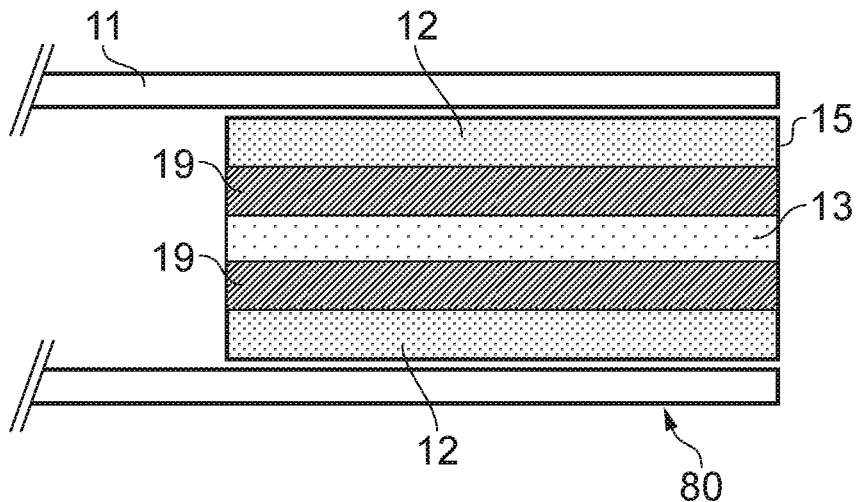

FIG. 8 represents in schematic cross-section view an inhaler component 80 that is a variation of the inhaler component 10 discussed above with reference to FIGS. 1A to 1C and shown in FIG. 2. Elements of the inhaler component 80 represented in FIG. 8 which are functionally similar to, and will be understood from, corresponding elements of the inhaler component 10 represented in FIG. 2 are identified with corresponding reference numerals. Only a portion of the inhaler component 80 in the vicinity of the inlet 15 is represented in FIG. 8, it being understood the remainder of the inhaler component may be provided in line with any of the other examples discussed herein. The inhaler component 80 represented in FIG. 8 differs from the inhaler component 10 represented in FIG. 2 by the manner in which the liquid vapor precursor material is fed to the susceptor/thermal store for heating. In the example described above, the vapor precursor material is stored in a cotton wadding which is generally in proximity to the thermal store. However, in the example of FIG. 8, the liquid vapor precursor material 12 is stored in an annular reservoir around the inside of the tube 11 and a wicking element 19, in this example comprising ceramic fibers, is arranged to draw the liquid vapor precursor material to the susceptor 13 for vaporization. The liquid vapor precursor material may be stored in an annular wadding material, e.g. of the kind discussed above with reference to the configuration of FIG. 2, or may comprise free liquid retained in an annular walled chamber into which the wicking element extends. In this regard, the arrangement of FIG. 8 may be considered to comprise a relatively high-porosity region for storing the bulk of the liquid vapor precursor material and a wicking element with a lower porosity for controlling the flow of liquid to the susceptor at a desired rate. It will be appreciated the wicking element may comprise other materials and forms, for example a porous rather than fibrous material, and may comprise a ceramic, metallic or any other suitable material, for example fiberglass. More generally, any material able to withstand the heat of the susceptor and capable of wicking the liquid vapor precursor material to the susceptor may be used. The inhaler component 80 of FIG. 8 may be used in conjunction with a base unit corresponding to that used with the inhaler component 10 of FIG. 2 and discussed above.

Figure 9:
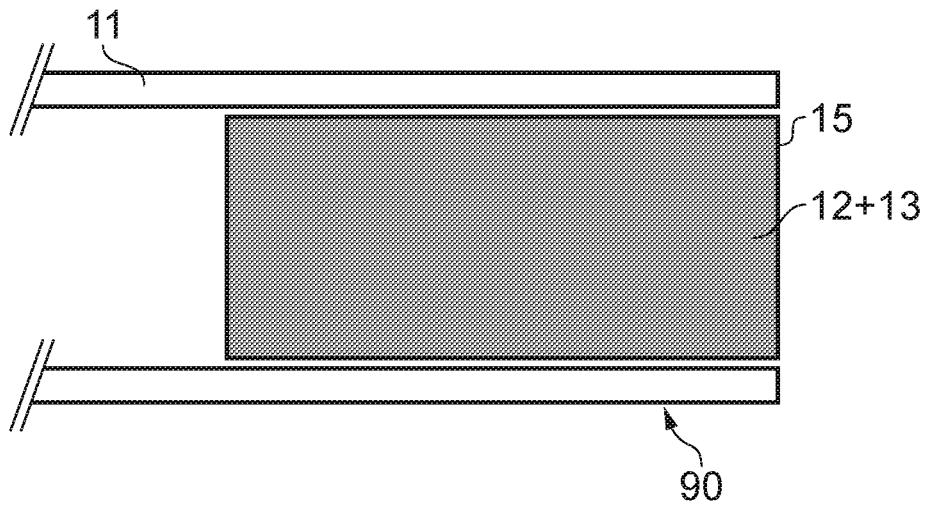

FIG. 9 represents in schematic cross-section view an inhaler component 90 which is yet another variation of the inhaler component 10 discussed above with reference to FIGS. 1A to 1C and shown in FIG. 2. Elements of the inhaler component 90 represented in FIG. 9 which are functionally similar to, and will be understood from, corresponding elements of the inhaler component 10 represented in FIG. 2 are identified with corresponding reference numerals. As for FIG. 8, only a portion of the inhaler component 90 in the vicinity of the inlet 15 is represented in FIG. 9, it being understood the remainder of the inhaler component may be provided in line with any of the examples discussed above. The inhaler component 90 represented in FIG. 9 differs from the inhaler component 10 represented in FIG. 2 by the arrangement of the thermal store/susceptor 13 and the vapor precursor material 12. In particular, the thermal store/susceptor 13 in the example of FIG. 9 comprises a fibrous metallic material, for example a wire wool/steel wool, and the vapor precursor material 12 comprises a gel coating on the fibers comprising the 13. This may be formed, for example, by simply dipping the fibrous susceptor 13 into a liquid form of the vapor precursor material which subsequently dries/cools to form a gel. The inhaler component 90 of FIG. 9 may be used in conjunction with a base unit corresponding to that used with the inhaler component 10 of FIG. 2 and discussed above. Thus, when the inhaler component 90 is received in the receiving zone of the base unit, current may be induced in the fibrous susceptor 13 causing it to heat, and so vaporize the gel vapor precursor material 12 coating the fibers comprising the susceptor 13 for inhalation when the inhaler component is withdrawn from the base unit.

Figure 10:
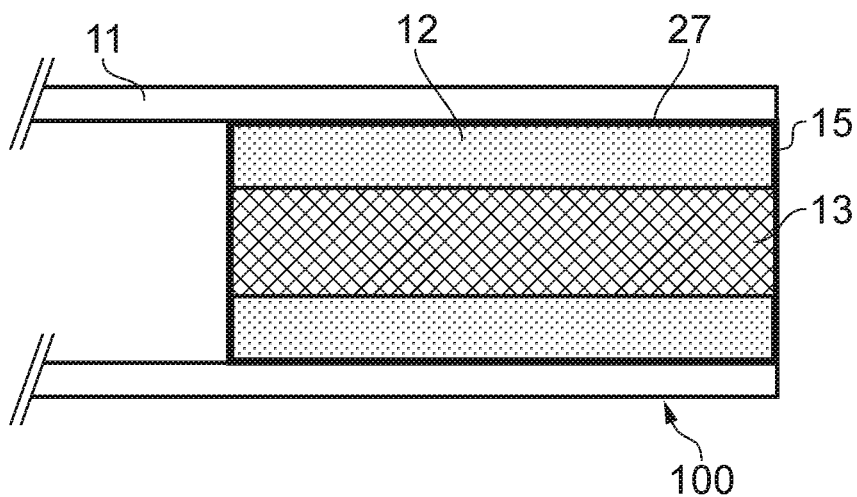

FIG. 10 represents in schematic cross-section view an inhaler component 100 which is yet another variation of the inhaler component 10 discussed above with reference to FIGS. 1A to 1C and shown in FIG. 2. Elements of the inhaler component 100 represented in FIG. 10 which are functionally similar to, and will be understood from, corresponding elements of the inhaler component 10 represented in FIG. 2 are identified with corresponding reference numerals. As for FIGS. 8 and 9, only a portion of the inhaler component 100 in the vicinity of the inlet 15 end of the inhaler component is represented in FIG. 10, it being understood the remainder of the inhaler component may correspond with any of the other examples discussed herein. The inhaler component 100 represented in FIG. 10 again differs from the inhaler component 10 represented in FIG. 2 by the arrangement of the thermal store/susceptor 13 and the vapor precursor material 12. In particular, in the arrangement represented in FIG. 10, liquid vapor precursor material 12 is stored in an annular walled chamber 27 rather than in a matrix of cotton wadding. The walled chamber 27 may, for example, comprise a generally tubular insert for locating within the tube housing 11 of the inhaler component 100, as schematically represented in FIG. 10, but in other implementations may be integrally formed with the housing 11. The susceptor in FIG. 10 comprises a generally planar metallic mesh (or other porous structure), e.g. a sintered metal fiber material generally in the form of a sheet. At least one edge of the susceptor extends into a corresponding slot in an inner wall of the chamber 27, thereby allowing the susceptor to wick liquid 12 from within the chamber 27 and so become wet. During use, the susceptor 13 is heated by an induction coil in a base unit of the kind discussed above so that liquid is vaporized from the surface of the susceptor 13 for inhalation by a user. Liquid which is vaporized from the susceptor 13 is replenished by wicking from the liquid in the surrounding chamber due to the porosity of the susceptor material itself. As already noted, it will be appreciated the specific size and shape of the susceptor 13 is not critical, but in the example of FIG. 10 it is a generally rectangular shape comprising sintered fibers of steel and has dimensions of around 25 mm×3.5 mm by 1 mm.

Figure 11:
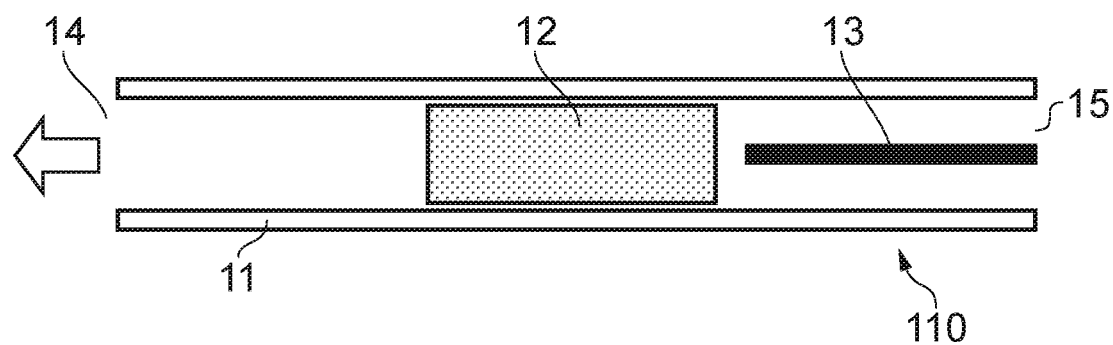

FIG. 11 represents in schematic cross-section view an inhaler component 110 that represents yet another variation of the inhaler component 10 discussed above with reference to FIGS. 1A to 1C and shown in FIG. 2. Elements of the inhaler component 110 represented in FIG. 11 which are functionally similar to, and will be understood from, corresponding elements of the inhaler component 10 represented in FIG. 2 are identified with corresponding reference numerals. The inhaler component 110 represented in FIG. 11 differs from the inhaler component represented in FIG. 2 in that the vapor precursor material 12 is not in direct thermal contact with the susceptor/thermal store 13, but is located upstream (i.e. between the susceptor/thermal store 13 and the mouthpiece outlet 14). Thus, in use, the susceptor is heated, for example using a base unit of the kind discussed above, and when a user inhales on the mouthpiece end 14, air is drawn through the air inlet and into the inhaler component 110 where it is heated by heat in the thermal store 13 so the heated air is drawn through/over the vapor precursor material to generate the vapor for inhalation. This configuration may in some respects be considered to correspond to a puff activated device in that when a user is not drawing air through the inhaler component 110 there is no (or at least significantly less) heat transferred to the vapor precursor material, and so less vaporization when the device is not being puffed. In another implementation, the inhaler component may be arranged so that the thermal store may be moved relative to the vapor precursor material so that these two elements may be brought into alignment/proximity to generate vapor, and removed from alignment/proximity to in effect turn off vapor generation. In this case the relative movement may be driven by user inhalation, for example with one or other of the thermal store or the vapor precursor material being moved by air flow in the inhaler component has a user draws on the inhaler component mouthpiece. In yet another implementation, a region surrounding the thermal store may be closed by a flap which is opened when a user inhales on the inhaler component. Thus, the area surrounding the inhaler may in effect be a closed space from which vapor cannot escape until a user inhales on the device to open the flap and draw out the vapor.

It will of course be appreciated the features of the various embodiments of the disclosure described herein can be combined. For example, a filter and flavor capsule of the kind represented in FIG. 7 can be provided for any of the configurations represented in FIGS. 2 to 6 and 8 to 11. Similarly a tobacco portion of the kind represented in FIGS. 3 to 6 can be included in any of the configurations represented in FIGS. 8 to 11. Furthermore, any of the vapor precursor material and thermal store configurations represented in FIGS. 8 to 11 may be used in conjunction with any of the arrangements set out in FIGS. 2 to 7. More generally, it will be appreciated there are a wide range of implementations that may be adopted in line with the underlying principle of using a base unit to provide energy to heat a thermal store for vaporizing a vapor precursor material in an inhaler component which is withdrawn from the base unit for use.

Furthermore, and as already noted, the base unit may adopt a range of different forms. For example, whereas in the example represented in FIGS. 1A to 1C the base unit comprises a single receiving zone in the form of a tubular opening, in other examples a base unit may comprise multiple receiving zones for simultaneously treating a corresponding plurality of inhaler components. Furthermore, the receiving zones may comprise configurations other than a tubular recess.

Figure 12:
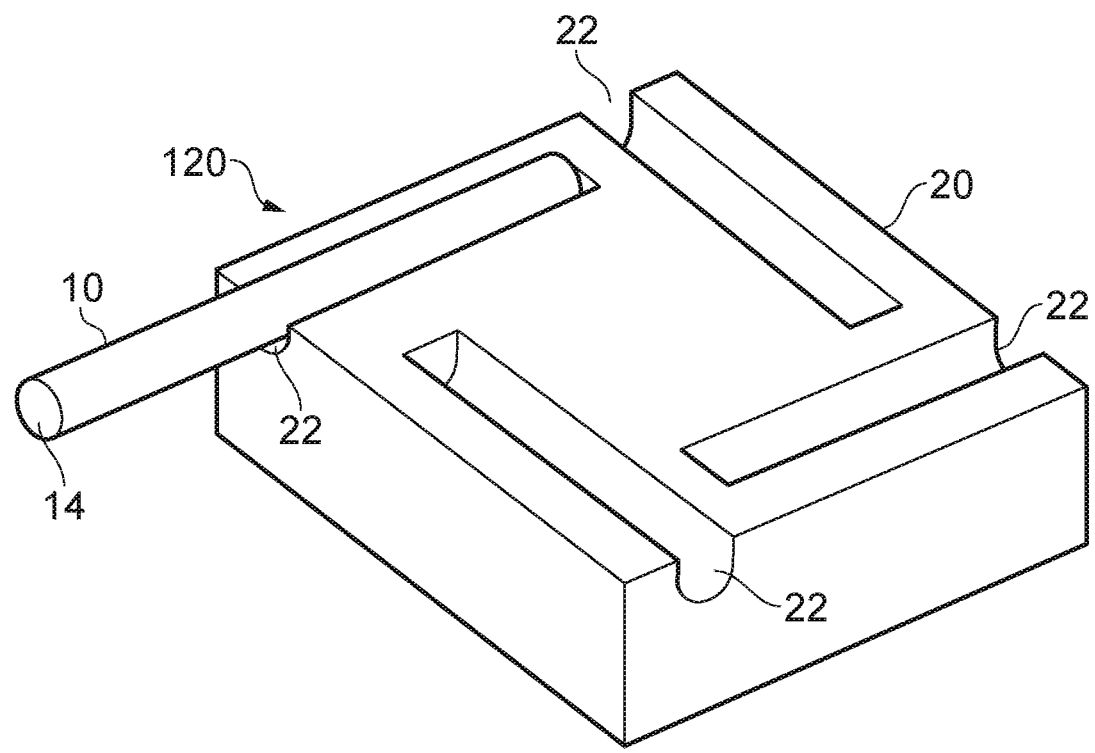
FIG. 12 represents in highly schematic perspective view a vapor provision system in accordance with certain other embodiments of the disclosure.

In this regard, FIG. 12 schematic represents a base unit 120 having a different design to the base unit schematically represented in FIGS. 1A to 1C. In this example the base unit 120 comprises four receiving zones 22 generally in the form of half-tube recesses in which an inhaler component (one example inhaler component 10 is shown in FIG. 12) may be laid. When an inhaler component is received in one of the receiving zones 22 its thermal store may be heated inductively in accordance with the principles described above. In this regard it will be appreciated the configuration of the induction coil will be different to that schematically represented in FIGS. 1A to 1C in that it will not completely surrounds the inhaler component, but will, in effect, be adjacent one side of the inhaler component. In this regard the induction coil may be a flat or curved coil. More generally the design and configuration of the induction coil may be chosen having regard to the well-established principles for inductive heating. For some geometries there may be a preferred orientation of the inhaler component with respect to the induction coil, and in this case the inhaler component may be marked to indicate the orientation to use (e.g. such that a decal on the inhaler component faces upwards or lined with a mark on the base unit). The base unit 120 represented in FIG. 12 may be provided with functionality of the kind discussed above for the base unit 20 represented in FIGS. 1A to 1C, albeit providing this functionality for a plurality of different receiving zones. Thus, the base unit 120 having a plurality of receiving zones may comprise a corresponding plurality of induction coils and activation sensors.

Thus, there has been described a vapor provision system comprising: an inhaler component and a base unit, wherein the inhaler component comprises a thermal store and a vapor precursor material; and the base unit comprises: a receiving zone for receiving the inhaler component; and a source of energy for heating the thermal store in the inhaler component when the inhaler component is located in the receiving zone such that heat is conducted from the heated thermal store to the vapor precursor material to vaporize at least a portion of the vapor precursor material to form a vapor for inhalation by a user when the inhaler component is removed from the receiving zone.

There has also been described a base unit for use in vapor provision system comprising the base unit and an inhaler component, wherein the base unit comprises a receiving zone for receiving the inhaler component and a source of energy for heating a thermal store in the inhaler component when the inhaler component is located in the receiving zone such that heat from the heated thermal store may be used to vaporize a portion of vapor precursor material to form a vapor for inhalation by a user when the inhaler component is removed from the receiving zone.

There has also been described an inhaler component for use in a vapor provision system comprising the inhaler component and a base unit, wherein the inhaler component comprises a thermal store arranged to be heated by a source of energy in the base unit when the inhaler component is received in a receiving zone of the base unit, such that heat from the heated thermal store may be used to vaporize a portion of vapor precursor material to form a vapor for inhalation by a user when the inhaler component is removed from the receiving zone.

The example embodiments described above have focused on approaches in which the base unit is configured to heat the thermal store in the inhaler component by electromagnetic induction. However, other techniques for transferring energy from the base unit to the thermal store can be used. For example, in some implementations the base unit may in effect comprise a hotplate/heater and the thermal store in the inhaler component may be arranged so that it is positioned in contact with/in proximity to the hotplate/heater when the inhaler component is placed in the receiving zone of the base unit so the thermal store is heated by thermal conduction. Other example approaches could involve optical heating of the thermal store when the inhaler component is placed in the base unit.

Furthermore, while some particular thermal store and vapor precursor material configurations have been described by way of example, it will be appreciated other configurations may be used. For example, rather than provide a thermal store in the form of a metallic sheet, the thermal store may have a block or rod shape, and may be solid or porous (e.g. comprising a metallic mesh, foam fibers or array of metallic particles). Furthermore, the thermal store need not be metallic, for example it may comprise an electrically conductive ceramic or a non-electrically conductive material in implementations which do not use inductive heating. Similarly, the vapor precursor material may adopt various form of liquid, solid, gel, paste or foam.

It will also be appreciated the base unit may for some implementations be provided with additional functionality. For example, in some cases the base unit may incorporate a means for measuring the temperature of the thermal store, for example based on detecting infrared radiation with a thermopile from the thermal store or using a thermocouple, or other temperature sensor. In this case the base unit may be configured to drive the transfer of energy to the thermal store of the inhaler component until an appropriate temperature is reached. In some implementations the inhaler components may be provided with an identifier, for example in the form of an RFID tag, which the base unit is configured to read. In such cases, the base unit may, for example, be configured to work only with certain inhaler components (e.g. inhaler components from a given supplier), or may be configured to operate differently for different types of inhaler components, example to heat differently depending on the identity of the inhaler component, for example to take account of different characteristics of vapor precursor materials or thermal store that may be used in different inhaler components.

Furthermore, in some examples the base unit may be configured to detect a characteristic of the inhaler component, e.g., a size or surface color or an electromagnetic characteristic of the susceptor, as it is inserted into the base unit, and to provide different amounts of energy to the thermal store based on this detection. For example, an inhaler component based on a liquid vapor precursor material may require less heat than an inhaler component based on a solid vapor precursor material so that an inhaler component based on a solid vapor precursor material has a larger thermal store. The base unit may be configured to detect the size of the thermal store (e.g. using conventional metal-detection techniques) and provide an appropriate amount of energy using the induction heating coil).

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A vapor provision system comprising: an inhaler component comprising a thermal store;
   a base unit comprising a receiving zone for receiving the inhaler component and a sensor for determining when the inhaler component is to be removed from the receiving zone; and
   a source of energy for heating the thermal store in the inhaler component when the inhaler component is located in the receiving zone such that heat from the heated thermal store is used to vaporize at least a portion of a vapor precursor material to form a vapor for inhalation by a user when the inhaler component is removed from the receiving zone, wherein the source of energy is configured to heat the thermal store in response to the sensor determining the inhaler component is to be removed from the receiving zone.

2. The vapor provision system of claim 1, wherein the sensor comprises a motion sensor for detecting when the inhaler component starts moving in the receiving zone.

3. The vapor provision system of claim 1, wherein the sensor comprises a proximity sensor for detecting when a user approaches the inhaler component when the inhaler component is in the receiving zone.

4. The vapor provision system of claim 1, wherein the sensor comprises a user activated switch.

5. The vapor provision system of claim 1, wherein the thermal store comprises an electromagnetic susceptor and the source of energy for heating the thermal store comprises an electromagnetic induction coil.

6. The vapor provision system of claim 1, wherein the source of energy for heating the thermal store comprises a heater arranged to thermally conduct heat to the thermal store when the inhaler component is located in the receiving zone.

7. The vapor provision system of claim 1, wherein the thermal store comprises at least one of: a metallic block, a metallic rod, a metallic sheet; a metallic mesh; a metallic foam; a metallic coil; metallic fibers; an array of metallic particles; or a ceramic.

8. The vapor provision system of claim 1, wherein the vapor precursor material comprises at least one of: a liquid; a solid; a gel, a paste, or a foam.

9. The vapor provision system of claim 8, wherein the vapor precursor material comprises a liquid stored in an absorbent material.

10. The vapor provision system of claim 8, wherein the vapor precursor material comprises a liquid in a reservoir and the inhaler component further comprises a wicking element for conveying liquid from the reservoir to the thermal store.

11. The vapor provision system of claim 10, wherein the wicking element comprises at least one of: a fibrous material, a porous ceramic material, disclosure a porous metallic material.

12. The vapor provision system of claim 1, wherein the inhaler component comprises a portion of tobacco in addition to the vapor precursor material that is heated by the thermal store.

13. The vapor provision system of claim 12, wherein the portion of tobacco is arranged so that the portion of tobacco is also heated by the thermal store during use.

14. The vapor provision system of claim 1, wherein the inhaler component further comprises a source of flavorant for imparting a flavor to the vapor inhaled by the user.

15. The vapor provision system of claim 14, wherein the source of flavorant comprises at least one sealed flavor capsule that may be selectively opened by a user to selectively impart the flavor to the vapor.

16. The vapor provision system of claim 1, wherein the thermal store is arranged between an air inlet for the inhaler component and the vapor precursor material so that when a user inhales on the inhaler component during use, air is drawn through the air inlet and past the thermal store for heating before passing the vapor precursor material.

17. The vapor provision system of claim 1, wherein the base unit comprises a plurality of receiving zones for receiving a plurality of inhaler components.

* * * * *

UNITED STATES PATENT AND TRADEMARK OFFICE
CERTIFICATE OF CORRECTION

| | |
|---|---|
| PATENT NO. | : 11,878,113 B2 |
| APPLICATION NO. | : 16/754502 |
| DATED | : January 23, 2024 |
| INVENTOR(S) | : Richard Hepworth et al. |

It is certified that error appears in the above-identified patent and that said Letters Patent is hereby corrected as shown below:

On the Title Page

Item (71), "London (SB)" should read --London (GB)--.

Signed and Sealed this
Ninth Day of April, 2024

Katherine Kelly Vidal
*Director of the United States Patent and Trademark Office*